(12) United States Patent
Ingenito (10) Patent No.: US 7,861,710 B2
(45) Date of Patent: Jan. 4, 2011

(54) RESPIRATORY ASSISTANCE APPARATUS AND METHOD

(75) Inventor: Edward P. Ingenito, Kingston, MA (US)

(73) Assignee: Aeris Therapeutics, Inc., Woburn, MA (US)

( * ) Notice: Subject to any disclaimer, the term of this patent is extended or adjusted under 35 U.S.C. 154(b) by 757 days.

(21) Appl. No.: 11/824,942

(22) Filed: Jul. 2, 2007

(65) Prior Publication Data

US 2008/0115787 A1 May 22, 2008

Related U.S. Application Data

(60) Provisional application No. 60/817,987, filed on Jun. 30, 2006, provisional application No. 60/818,361, filed on Jul. 2, 2006.

(51) Int. Cl.
*A61M 11/00* (2006.01)

(52) U.S. Cl. ............................. 128/200.24; 128/205.13; 128/205.14

(58) Field of Classification Search ............ 128/200.24, 128/204.18, 204.21, 204.22, 205.13, 205.14
See application file for complete search history.

(56) References Cited

U.S. PATENT DOCUMENTS

| | | | |
|---|---|---|---|
| 5,107,830 A | 4/1992 | Younes et al. | |
| 5,497,767 A * | 3/1996 | Olsson et al. ......... | 128/205.13 |
| 5,520,192 A | 5/1996 | Kitney et al. | |
| 5,906,203 A * | 5/1999 | Klockseth et al. ...... | 128/205.24 |
| 6,015,388 A | 1/2000 | Sackner et al. | |
| 6,131,571 A * | 10/2000 | Lampotang et al. .... | 128/204.21 |
| 6,165,105 A | 12/2000 | Boutellier et al. | |
| 6,273,088 B1 | 8/2001 | Hillsman | |
| 6,328,036 B1 * | 12/2001 | Emtell et al. ........... | 128/205.14 |
| 6,390,091 B1 | 5/2002 | Banner et al. | |
| 6,463,928 B1 * | 10/2002 | Buisson ................. | 128/203.12 |
| 6,571,796 B2 | 6/2003 | Banner et al. | |
| 6,796,305 B1 | 9/2004 | Banner et al. | |
| 6,820,618 B2 | 11/2004 | Banner et al. | |
| 6,929,006 B2 * | 8/2005 | Kruger et al. .......... | 128/204.22 |
| 7,066,173 B2 | 6/2006 | Banner et al. | |
| 7,210,478 B2 | 5/2007 | Banner et al. | |
| 7,425,201 B2 | 9/2008 | Euliano et al. | |
| 2002/0104537 A1 | 8/2002 | Banner et al. | |
| 2005/0115561 A1 | 6/2005 | Stahmann et al. | |
| 2006/0283451 A1 * | 12/2006 | Albertelli ............... | 128/204.28 |
| 2007/0000494 A1 | 1/2007 | Banner et al. | |
| 2007/0028921 A1 | 2/2007 | Banner et al. | |
| 2007/0232951 A1 | 10/2007 | Euliano et al. | |
| 2008/0115787 A1 | 5/2008 | Ingenito | |
| 2008/0178880 A1 | 7/2008 | Christopher et al. | |
| 2008/0178882 A1 | 7/2008 | Christopher et al. | |

* cited by examiner

*Primary Examiner*—Steven O Douglas
(74) *Attorney, Agent, or Firm*—Foley Hoag LLP (57) ABSTRACT

A hand-held apparatus that delivers pressurized breathing gas to the airway of a patient, thereby creating positive end expiratory pressure (PEEP) and reducing respiratory muscle fatigue. The apparatus includes a deformable reservoir, a breathing interface, and a pressure relief valve. The apparatus may include a means for creating fluid communication between the deformable reservoir and a source of pressurized breathing gas. The apparatus may also include an adjuster that allows a user to vary the pressure of the breathing gas contained in the deformable reservoir.

34 Claims, 10 Drawing Sheets

RESPIRATORY ASSISTANCE APPARATUS AND METHOD

RELATED APPLICATIONS

This application claims the benefit under 35 U.S.C. §119 (e) from U.S. provisional application Ser. No. 60/818,361, filed Jul. 2, 2006, and Ser. No. 60/817,987 filed, Jun. 30, 2006, the contents of both of which are incorporated herein by reference in their entirety.

BACKGROUND OF INVENTION

1. Field of Invention

The invention relates to methods and devices for assisting respiration in patients suffering from auto positive end expiratory pressure (auto-PEEP).

2. Background

Gas exchange in the human lungs occurs through a series of pressure changes that occur during the inspiration and expiration portions of the breathing cycle. During inspiration, the diaphragm descends to subsequently produce negative pressure (relative to atmospheric pressure) in the alveoli. With atmospheric pressure at the beginning of the airway (i.e., at the nose and mouth) and negative pressure in the alveoli, the pressure gradient causes air to be drawn into the airway toward the alveoli. During expiration, positive pressure (relative to atmospheric pressure) is created in the alveoli through the ascension of the diaphragm (i.e., respiratory muscles contract) and elastic recoil of the lung. The pressure gradient between the alveoli and the atmosphere causes expired breath to be expelled from the airway. During normal expiration, the pressure in the alveoli continues to decrease as breath is expired. At the end of the expiration phase, the pressure in the alveoli is equal to atmospheric pressure, and the inspiration phase begins.

In patients with lung disease, an obstruction in the airway prevents the pressure in the alveoli from decreasing to atmospheric pressure. That is, after the patient's diaphragm has fully ascended and the lung has fully recoiled, the pressure in the patient's alveoli remains above atmospheric pressure. This condition is known as auto-positive end expiratory pressure (auto-PEEP).

In patients suffering from auto-PEEP, the patient's diaphragm has to descend further (i.e., do more work) to create the negative pressure drop needed to inhale air from the atmosphere. For example, if the pressure in the alveoli at the end of the expiratory phase is 10 cm $H_2O$ above atmospheric pressure and the pressure in the alveoli needed for inspiration is $-5$ cm $H_2O$ relative to the pressure at the airway, the patient's diaphragm will have to descend to produce a net pressure change of $-15$ cm $H_2O$ in the alveoli. By contrast, if the pressure in the alveoli at the end of the expiratory phase is normal (atmospheric pressure, 0 cm $H_2O$), the diaphragm will only have to descend to produce a net pressure change of $-5$ cm $H_2O$. By requiring the diaphragm to descend further to achieve inspiration of air, the auto-PEEP resulting from lung disease causes fatigue. In extreme cases, the auto-PEEP becomes so severe (i.e., the pressure in the alveoli at the end of expiration is so high) that the diaphragm cannot descend far enough to create the negative pressure required for inspiration. Without the ability to inhale fresh air, the patient suffers respiratory distress.

SUMMARY OF INVENTION

Aspects of the invention relate to methods and devices for alleviating respiratory difficulties in patients suffering from auto-PEEP. Methods and devices of the invention can be used to provide positive pressure at the nose and/or mouth of a patient, thereby alleviating breathing difficulties in a patient suffering from auto-PEEP or similar condition characterized by abnormally high alveolar pressures (e.g., at the end of expiration).

To alleviate fatigue and respiratory distress in patients suffering from auto-PEEP, positive pressure can be applied at the patient's nose or mouth. Positive pressure at the patient's nose or mouth reduces the amount of work required of the patient's descending diaphragm during the inspiration phase.

In the example above, the pressure in the patient's alveoli at the end of expiration was 10 cm $H_2O$ (i.e., the patient's auto-PEEP pressure was 10 cm $H_2O$). Consequently, in that example, the patient's diaphragm descended to produce $-10$ cm $H_2O$ pressure differential to overcome the auto-PEEP and then descended further to produce an additional $-5$ cm $H_2O$ pressure differential to allow inspiration of air. Put differently, the patient can only begin inspiration once the patient's diaphragm descended to produce a negative 15 cm $H_2O$ pressure differential between the patient's upper airway and the alveoli.

By applying pressure at the patient's upper airway, the patient's diaphragm is not required to descend as far to overcome the auto-PEEP and initiate breathing. Continuing with the example from above, if a positive pressure of 5 cm $H_2O$ is applied at the patient's upper airway, the patient will begin inspiration when the patient's diaphragm descends to produce an additional $-10$ cm $H_2O$ pressure drop between the alveoli and the upper airway. That is, a $-15$ cm $H_2O$ pressure differential between the alveoli and the upper airway is still required to initiate inspiration, but the positive pressure applied at the upper airway alleviates some of the work required to achieve this pressure differential.

The following description details devices and methods for alleviating respiratory difficulties associated with auto-PEEP.

BRIEF DESCRIPTION OF DRAWINGS

The accompanying drawings are not intended to be drawn to scale. For purposes of clarity, not every component may be labeled in every drawing. The drawings illustrate certain embodiments of the invention and are not intended to be limiting. In the drawings:

FIG. 1 illustrates an embodiment of a respiratory of a respiratory assistance device (1) connected to a source of breathable gas (310—not drawn to scale)

FIG. 3 illustrates an embodiment of a respiratory assist device (300) attached to a source of breathable gas (310—not drawn to scale) and a deformable member (320—not drawn to scale)

FIG. 4 illustrates an embodiment of a respiratory device sub-assembly (400)

FIG. 5 illustrates an embodiment of a respiratory assist device body (410)

FIG. 6 illustrates an embodiment of a of a respiratory assist device cover (420)

FIG. 7 illustrates an embodiment of a respiratory assist device valve.

FIG. 8 illustrates an embodiment of a respiratory assist device valve housing (430)

It should be appreciated that the different component parts and features illustrated in the Figures are not intended to be limiting. Furthermore, one or more features (e.g., structures or functional components) described in connection with any one of the Figures herein may be combined with one or more features (e.g., structures or functional components) described in connection with any of the other Figures herein. For example, one or more of the features of FIGS. 1-2 may be combined with one or more of the features of any of FIGS. 3-9. These and other aspects of the invention are described in more detail below.

DETAILED DESCRIPTION

The present invention relates to an apparatus and method for delivering positive end expiratory pressure (PEEP) to the airway of a patient. An exemplary application of this invention may be for reducing respiratory muscle fatigue, thereby lowering the risk of respiratory failure in patients with asthma and chronic pulmonary disease (COPD). In some embodiments, the gas pressure delivered from the apparatus to the airway of the patient may be selected based on a predetermined threshold pressure shown to assist patients with auto-PEEP. However, a patient may regulate the gas pressure as described herein. Accordingly, the invention may be suitable for delivering pressurized breathing gas to the airway of a patient.

Aspects of the invention relate to a handheld device that forms a sealed system when placed in fluid communication with the airway of a patient and contains pressurized breathing gas within a deformable reservoir. The deformable reservoir expands to contain approximately one tidal volume pressurized breathing gas (e.g., between 0.5 and 2 tidal volumes, or smaller or larger volumes, for example between about 0.5 and about 5 tidal volumes, or smaller or larger volumes) and then subsequently stops expanding to allow pressure to build up within the deformable reservoir. The device allows pressure to build up within the deformable reservoir up to a desired pressure and subsequently vents the pressurized breathing gas to the atmosphere when the pressure in the deformable reservoir is above the desired pressure. Through venting pressure to the atmosphere, the device functions to deliver a constant supply of pressurized breathing gas to the airway of a patient suffering from lung disease. It should be appreciated that aspects of the invention are useful for human patients. However, certain methods and devices may be adapted for use to assist in the respiration of other mammals or animals suffering from respiratory difficulty associated with abnormally high alveolar pressures.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the description that follows, the word "gas" is meant to include matter characterized by relatively high compressibility and a readiness to flow. Accordingly, in the discussion herein, gas includes fluids of homogenous composition (e.g., oxygen at ambient pressure and temperature) as well as mixtures of fluids (e.g., air at ambient pressure and temperature). Furthermore, the word gas encompasses incompressible matter suspended within a highly compressible medium. For example, gas encompasses liquid water or surfactant droplets suspended in air.

As used herein, the word "pressurized" is meant to describe a state of matter wherein the pressure of a gas is greater than atmospheric pressure (e.g., 1033 cm $H_2O$ at sea level). Moreover, quantities of pressure will be herein expressed relative to atmospheric pressure. Thus, in the discussion that follows, a volume containing air at 5 cm $H_2O$ will be termed pressurized.

The words "deform" and "deformation" will refer to either a positive or negative change in at least one dimension of a reservoir. Unless otherwise specified, deformation will be measured relative to the dimensions of the reservoir containing gas at ambient temperature and pressure (i.e., the undeformed reservoir). For example, if the reservoir contains 0.25 L of air at atmospheric pressure and 0.75 L of air at 10 cm $H_2O$, the reservoir deformed by a volume of 0.5 L (i.e., the difference between 0.75 L and 0.25 L). Furthermore, unless otherwise specified, deformation of a reservoir will be the result of a change in pressure of the pressurized gas acting on the reservoir. That is, it will be presumed that deformation of the reservoir is not the result of manual manipulation of the reservoir (e.g., squeezing the volume).

The term "pressurized breathing gas" (hereinafter PBG) will refer to breathing gas that originates from a source of PBG and flows toward the airway of a patient. A positive pressure gradient between the source of PBG and the airway of the patient causes PBG to flow toward the airway of the patient. As used herein, PBG refers to oxygen mixed with at least one inert gas in a volume ratio that is suitable for normal human respiration. Accordingly, PBG may be air, may include oxygen, heliox, and/or combinations thereof. However, it should be appreciated that PBG may be any gas suitable for breathing. In some embodiments, the oxygen content of PBG may be modified (e.g., optimized for certain diseased patients or conditions). PBG may further include a volume fraction of the expired breath of the patient. As discussed below, it is one aspect of the present invention to limit the concentration of expired breath in the PBG such that the PBG remains suitable for normal human respiration.

The term "venting pressure" will refer to the maximum pressure in the apparatus just before the PBG is exhausted from the apparatus to the environment. As used herein, the magnitude of venting pressure will be expressed relative to atmospheric pressure. Therefore, a venting pressure of 0 cm $H_2O$ corresponds a venting pressure equal to atmospheric pressure.

In one illustrative embodiment, the hand-held PEEP device includes a deformable reservoir, a breathing interface, and a pressure relief valve. The deformable reservoir is in fluid communication with an external source of pressurized breathing gas, and the deformable reservoir may function to contain a volume of the pressurized breathing gas originating from the external source. The deformable reservoir is in further fluid communication with a breathing interface. In use, the breathing interface is in fluid communication with the airway of the patient.

It should be appreciated that various combinations of the above-described embodiments of the present invention can be employed together, but several aspects of the present invention are not limited in this respect. Therefore, although the specific embodiment disclosed in the figures and described in detail below employs particular combinations of the above-discussed features of the present invention, it should be appreciated that the present invention is not limited in this respect, as the various aspects of the present invention can be employed separately, or in different combinations. Thus, the particular embodiment described in detail below is provided for illustrative purposes only.

Figure shows an illustrative embodiment of a respiratory assistance apparatus 1 in accordance with the present invention. This embodiment of the invention incorporates many of the inventive aspects discussed herein.

Figure 1A:
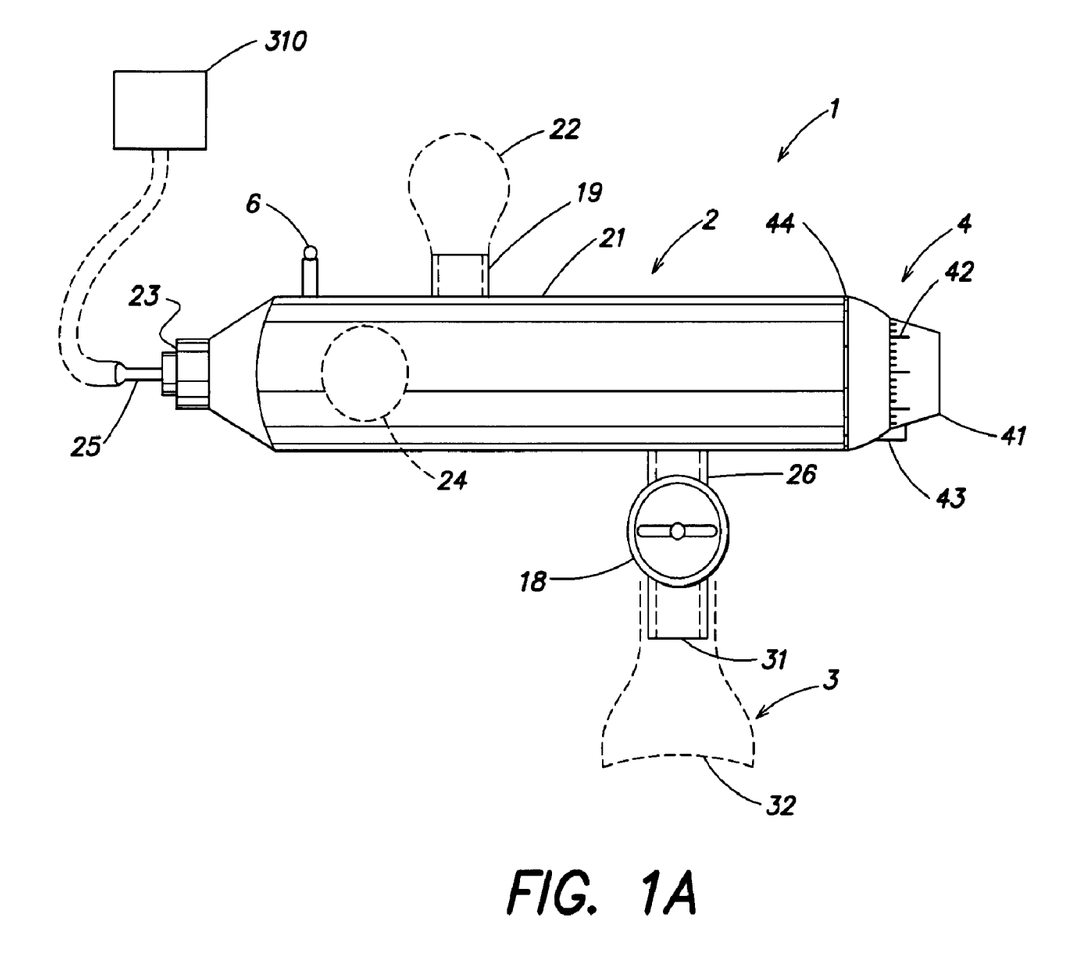
FIGS. 1A, 1B and 1C show a perspective view and left and right side views respectively.

FIG. 1A is a perspective view of a respiratory assistance apparatus 1. As shown in the figure, the respiratory assistance apparatus 1 includes a deformable reservoir 2, a breathing interface 3, and a pressure relief valve 4.

As shown in FIG. 1A, the deformable reservoir 2 may include a rigid section 21 and a deformable section 22. The rigid section 21 may be formed of any of numerous inelastic materials or a combination of inelastic materials that are capable of withstanding the pressures that will be allowed to build up within the deformable reservoir 2. Thus, for example, rigid section 21 may be formed of polyproplylene, nylon, polyvinyl chloride (PVC) or any combination thereof. In a preferred embodiment, at least a portion of the deformable reservoir 2 is transparent to facilitate in-use inspection of the respiratory assistance apparatus 1.

Rigid section 21 includes at least one opening such that the rigid section 21 may be coupled to the deformable section 22. However, it should be recognized that the rigid section 21 may include any number of openings to place the rigid section 21 in fluid communication with the other components of the apparatus. In one embodiment, rigid section 21 may include a tee-connector to facilitate coupling the rigid section 21 to the deformable section 22, the breathing interface 3 (e.g., a mouthpiece, a nosepiece, a combination thereof, a face mask, or other suitable breathing interface), and a source of PBG 310. Similarly, in another embodiment, rigid section 21 may include a cross-shaped connector to facilitate coupling the rigid section 21 to the deformable section 22, the breathing interface 3, the pressure relief valve 4, and the source of PBG 310.

The deformable section 22 of the deformable reservoir 2 may be constructed of any of numerous deformable materials or combinations of deformable materials that change shape to vary the volume of PBG stored in the deformable reservoir 2. For example, deformable section 22 may be formed of a thin film of latex rubber. The deformable section 22 may be any of numerous shapes in the undeformed position. Similarly, the deformable section 22 may be any of numerous shapes in the deformed position. In one embodiment, the deformable section 22 is a balloon that inflates to accept PBG and deflates to expel PBG. In another embodiment, the deformable section 22 is a diaphragm that flexes to accept PBG into the deformable reservoir 2 and relaxes to expel PBG from the deformable reservoir 2.

In some embodiments, one or more components (e.g., one or more rigid components) may be molded (e.g., injection molded plastic). In some embodiments, two or more of the different components described herein may be manufactured as a single molded part. In other embodiments, individual components described herein may be manufactured in the form of two or more different molded parts. In some embodiments, different parts may be attached fixedly or reversibly, or a combination thereof, after molding to form a respiratory assist device or a part thereof. In some embodiments, one or more components of a device or apparatus described herein may be provided as separate parts (e.g., as replacement parts to replace broken, used, or defective parts; or as components that can be individually sterilized, etc.).

In one aspect of the invention, the deformable section 22 may be constructed such that the difference between the volume of the deformable section 22 in the deformed and undeformed states is approximately equal to or slightly greater than the tidal volume of a human breath. That is, the deformable reservoir 2 may be capable of expanding to contain a volume of PBG that is approximately equal to the tidal volume of a human breath. Accommodating approximately one tidal volume of pressurized gas in the deformable section 22 ensures that the patient will not be starved of pressurized breathing gas during episodes of sporadic breathing (e.g., gasping for breath). However, smaller or larger volumes may be used for deformable section 21.

In one embodiment, the deformable section 22 may be deformable to contain approximately 500 ml of PBG (e.g., at a predetermined pressure), the approximate tidal volume of an adult human breath. In another embodiment, the deformable section 22 may be deformable to contain approximately 10 ml, the approximate tidal volume of an infant human breath. In still another embodiment, the maximum volume of the deformable section 22 may be adjustable to any volume between 10 ml and 500 ml. However, smaller or larger volumes also may be used (e.g., about 1 liter, about 1.5 liters, about 2 liters or more) depending on the application.

In a preferred embodiment, the elasticity of the deformable reservoir 2 may be selected such that the deformable reservoir 2 expands to contain a desired volume of pressurized breathing gas (e.g., approximately a tidal volume) but does not expand beyond the desired volume, allowing pressure to build up within the deformable reservoir 2.

It should be noted that the deformable reservoir 2 may be constructed without a rigid section 21. That is, the deformable reservoir 2 may be constructed entirely of elastic material that will change shape in response to changes in the pressure of the gas contained therein. This embodiment may be particularly useful for minimizing the total size of the respiratory assistance apparatus 1, thereby making the respiratory assistance apparatus 1 more amenable to handheld use.

As shown in FIG. 1A, the deformable reservoir 2 may also include at least one opening 23 in fluid communication with the external source of pressurized breathing gas. In one embodiment, the opening 23 has an open area that does not substantially restrict the flow rate of pressurized breathing gas from the external source. In another embodiment, the opening 23 may include a porous filter that prevents unwanted matter (e.g., airborne particulates) from entering the respiratory assistance apparatus 1. In still another embodiment, the opening 23 may include a one-way check valve. In this embodiment, the one-way check valve may be arranged to permit PBG to flow into the deformable reservoir 2 when the pressure of the PBG exceeds the pressure within the deformable reservoir 2. Conversely, in the aforementioned configuration, the one-way check valve may prevent gas within the deformable reservoir 2 from flowing back toward the source of PBG 310 when the pressure at the PBG source is lower than that of the gas in the deformable reservoir 2.

As shown in FIG. 1A, the deformable reservoir 2 may also include at least one secondary orifice 24 to allow the deformable reservoir 2 to be placed in fluid communication with an external apparatus (not shown). In one embodiment, the external apparatus may be a nebulizer or a metered dose inhaler (MDI) (e.g., of a type known in the art). The external apparatus may be releasably coupled to the deformable reservoir 2 such that the contents of the external apparatus are delivered to the respiratory assistance apparatus 1 via the secondary orifice 24.

The external apparatus may be releasably coupled to the deformable reservoir 2 by any of several methods. In one embodiment, an external apparatus is releasably coupled to the deformable reservoir by an interference fit between the secondary orifice 24 and a mating section on the external apparatus. In another embodiment, an external apparatus is releasably coupled to the deformable reservoir 2 by a threaded screw arrangement of the type known in the art.

Secondary orifice 24 may include a one-way check valve. The one-way check valve may be arranged to permit the flow of fluid from the external apparatus to the deformable reservoir 2 but to prevent PBG from exhausting through the secondary opening 24. With a one-way check valve preventing the flow of PBG out of the secondary orifice 24, an external apparatus may be attached and detached to the secondary orifice 24 while the apparatus is in use.

In one embodiment, the one-way check valve is mechanically moved to the open position when an external apparatus is coupled to the secondary orifice 24. In another embodiment, the one-way check valve is moved to the open position by pressurized fluid exiting from the external apparatus.

It should be recognized that the secondary orifice 24 may be located at any position on the respiratory assistance apparatus 1, provided that the secondary orifice 24 places the external apparatus in fluid communication with the deformable reservoir 2. In one embodiment, the centerline of the secondary opening 24 is axially aligned with the centerline of the breathing interface 3. Aligning the secondary opening 24 with the breathing interface may be useful in directing the contents of the external apparatus toward the breathing interface 3. Directing the contents of the external apparatus toward the breathing interface 3 may, in turn, be useful for ensuring that medicine from the external apparatus neither collects on the walls of the deformable reservoir nor exits the respiratory assistance apparatus 1 through the pressure relief valve 4.

As secondary orifice 24 may also be used to remove condensation from the respiratory assistance apparatus 1. In one embodiment, the bottom of the deformable reservoir 2 may be pitched toward the secondary opening 24 such that condensation collected on the walls of the deformable reservoir 2 is pushed toward the secondary opening 24 by gravity and/or the flow of PBG. The respiratory assistance apparatus 1 may further include a collection reservoir wherein condensation is collected and ultimately removed from the respiratory assistance apparatus 1.

The deformable reservoir 2 may also include a connector 25 to create releasable, leak-tight connection between the deformable reservoir 2 and the source of PBG 310. In one embodiment, the connector 25 may be a threaded connector that can be screwed together with the source of PBG 310 to establish fluid communication between the deformable reservoir and the source of PBG 310. In another embodiment, the connector 25 may be an interference fit between the deformable reservoir 2 and the source of PBG 310. For example, the connector 25 may include a tapered barbed tube connector of the type known in the art. In this configuration, a tube from the source of PBG 310 may be slid over the tapered barbed tube connector, whereby the barbs of the tube connector form an interference fit with the inner surface of the tube from the source of PBG 310.

Of course, it should be recognized that the deformable reservoir 2 may be placed in fluid communication with the source of PBG 310 through a permanent, leak-tight connection. For example, a continuous length of flexible tubing may be used to connect the deformable reservoir 2 to the source of PBG 310.

The source of PBG 310 may include a pressurized bottle of gas and a flow rate control valve. In a preferred embodiment, the pressurized bottle of gas is of the type commonly used in medical applications such that the mixture of PBG is medical grade purity and has a known volumetric composition. In use, the flow rate control valve may regulate the flow of PBG from the pressurized tank to the deformable reservoir 2. In addition, the flow rate control valve may serve to stop the flow of PBG from the pressurized tank to the deformable reservoir 2.

The source of PBG 310 may also include a one-way pump that increases the gas pressure within the deformable reservoir 2 by drawing air from the atmosphere into the deformable reservoir. The atmospheric air drawn into the deformable reservoir 2 will act to increase the pressure inside of the deformable reservoir 2 and, as such, will serve to provide PEEP to the airway of the patient. In one embodiment, the pump is hand operated to facilitate portability of the entire apparatus. It should be appreciated that any other device or means for providing breathing gas under positive pressure may be used. Any suitable positive pressure may be used. For example, positive pressures between about 0.5 and about 50 cm H2O or equivalent thereof may be used. However, higher pressures may be used for certain applications (e.g., between about 50 and about 100 cm H2O or higher).

The respiratory assistance apparatus 1 may include any of several coating layers attached to at least a portion of the inner surface of the deformable reservoir 2. For example, the inner surface of the deformable reservoir 2 may include an antibacterial coating to lower the risk of delivering bacteria to the airway of the patient. The inner surface of the deformable reservoir 2 may further include a coating of medicine, whereby the coating detaches from the inner surface of the deformable reservoir 2 at a predictable rate such that the medicine may be delivered to the patient over an extended period of time.

As shown in FIG. 1A, the breathing interface 3 includes a first opening 31 in fluid communication with a second opening 32. The breathing interface 3 may be constructed of any of a number of materials that can be safely placed in physical contact and fluid communication with the oral and nasal regions of the patient. Thus, for example, the breathing interface may be formed from soft silicone or PVC. In one embodiment, at least a portion of the breathing interface 3 may be formed of transparent material.

As shown in FIG. 1A, the breathing interface 3 may be a mask designed to fit over the mouth and nose of the patient. The mask may be of the type commonly used in medical applications requiring the delivery of gas to the airway of the patient. In another embodiment, the breathing interface 3 may be a mouthpiece that fits into the mouth of the patient. In this configuration, a leak tight seal may be formed as the patient's mouth fits over the mouthpiece. The mouthpiece may be of the type commonly used as mouthpieces for MDIs.

FIG. 1A also shows that the deformable reservoir 2 may include at least one conduit 26 to connect the breathing interface 3 and the deformable reservoir 2 in fluid communication. The conduit 26 may be any of numerous shapes and dimensions and may also include a flexible section. In one embodiment, the dimensions of the conduit 26 may be sized such that the pressure drop of gas flowing across the conduit is minimal (i.e., less than 1%) compared to the overall pressure of the PBG contained in the deformable reservoir 2. In another embodiment, the conduit 26 may include a length of flexible cylindrical tubing to facilitate placing the breathing interface in fluid communication with the oral and/or nasal passages of the patient.

The first opening 31 may be placed in fluid communication with the deformable reservoir 2 by mechanically affixing the first opening 31 to the deformable reservoir 2 through any of a number of means known in the art. For example, the first opening 31 may be mechanically affixed to the deformable reservoir 2 through the use of an adhesive (e.g., glue), sonic welding, or thermal welding. In this embodiment, the breathing interface 3 and the deformable reservoir 2 are attached when the respiratory assistance apparatus 1 is manufactured and are not detachable by the user.

In another embodiment, the breathing interface 3 and at least a portion of the deformable reservoir 2 may be formed as a single molded plastic component. For example, the rigid section 21 and the breathing interface 3 may be formed as a single molded plastic component. Forming the breathing interface 3 and a portion of the deformable reservoir 2 from a single molded plastic component may improve the durability of and facilitate assembly of the respiratory assistance apparatus 1.

In still another embodiment, the first opening 31 may be placed in fluid communication with the deformable reservoir 2 by releasably attaching the breathing interface 3 to the deformable reservoir 2. In this embodiment, the first opening 31 may be releasably attached to the deformable reservoir 2 through an interference fit. For example, the first opening may include a circular open area with an inner radius dimensioned to fit tightly over the outer radius of conduit 25. In this embodiment, the first opening 31 may also be screwed to the deformable reservoir 2. If the first opening 31 is screwed to the deformable reservoir 2, the respiratory assistance apparatus may further include a washer. By placing the washer at the interface of the connection between first opening 31 and the deformable reservoir 2, a leak tight seal may be achieved.

In use, the second opening 32 of the breathing interface 3 is in fluid communication with the airway of the patient. The second opening 32 may be constructed to form a leak tight seal between the breathing interface 3 and the patient when the apparatus is in use. In particular, the breathing interface 3 may be constructed to form a leak tight seal with the mouth and/or nose of the patient. For example, the breathing interface may include a strap that holds the breathing interface 3 in place while the apparatus is in use.

The second opening 32 may also include a cushion layer to reduce the leak rate of breathing gas and improve the comfort of the patient when the device forms a leak tight seal with the mouth and/or nose of the patient. For example, if the breathing interface 3 is designed to fit over the nose and mouth of the patient, the second opening 32 may be lined with foam rubber such that the foam rubber contacts the patient's skin to form a leak tight seal.

As shown in FIG. 1A, the pressure relief valve 4 is in fluid communication with the deformable reservoir 2 and may be coupled to the deformable reservoir 2 through a secondary orifice 24. In one embodiment, the pressure relief valve 4 may be screwed into a secondary orifice 24. In a preferred embodiment, the pressure relief valve 4 may be screwed into a secondary orifice 24 positioned along the rigid section 21.

A washer 44 may be positioned between the pressure relief valve 4 and the deformable reservoir 2. The washer 44 may be used to create a leak tight seal between the pressure relief valve 4 and the deformable reservoir 2. The washer may be constructed of any of numerous materials including nylon and soft rubber.

FIG. 1A also shows that the pressure relief valve 4 may include an adjuster 41 to control the venting pressure of the PBG contained in the deformable reservoir 2. The adjuster 41 may be calibrated such that movement of the adjuster relative to an indicator marker 42 produces a known change in the venting pressure of the deformable reservoir 2. For example, the adjuster 41 may be marked from 0 to 50 cm $H_2O$ in 5 cm $H_2O$ increments such that a marking on the adjuster 41 may be aligned with the indicator marker 42 to achieve the appropriate venting pressure in the apparatus. Thus, continuing this example, a user may select a venting pressure of 10 cm $H_2O$ by moving the adjuster 41 such that the marker reading "10 cm $H_2O$" on the adjuster 41 is aligned with the indicator marker 42. In one embodiment, the adjuster 41 may be a rotatable dial that is turned in one direction to increase the venting pressure and turned in another direction to decrease the venting pressure of the deformable reservoir 2.

The pressure relief valve 4 may also include a lock 43 to hold the adjuster 41 in place and, therefore, hold the venting pressure constant while the apparatus is in use. The lock 43 may be any of several mechanisms known in the art suitable to prohibit the position of the adjuster 41 from changing when the lock 43 is engaged with the adjuster 41.

In normal use, when the pressure contained in the deformable reservoir 2 falls below the selected venting pressure, the pressure relief valve 4 opens to vent PBG to the atmosphere. When the pressure contained in the deformable reservoir 2 subsequently falls below the selected venting pressure, the pressure relief valve closes to allow the pressure of PBG to again build up inside of the deformable reservoir. The opening and closing pressures of the pressure relief valve 4 may be the same. Alternatively, the closing pressure of the pressure relief valve 4 may be lower than the opening pressure of the pressure relief valve 4.

As shown in FIG. 1A, the apparatus of the present invention may further include a safety vent 6. The safety vent 5 may protect the patient if the pressure relief valve 4 should fail to vent PBG to the atmosphere at the desired venting pressure. That is, the safety vent 6 may ensure that unsafe PBG pressures are never delivered to the airway of the patient, thereby avoiding potential damage to the alveoli.

In a preferred embodiment, the safety vent 6 may be constructed and arranged to vent PBG to the atmosphere at a venting pressure that is higher than the venting pressure of the pressure relief valve 4. For example, the safety vent 6 may be constructed and arranged to vent PBG to the atmosphere at a venting pressure of 60 cm $H_2O$ while the pressure relief valve 4 is designed to have a maximum venting pressure of 55 cm $H_2O$. In this example, should the pressure relief valve 4 fail to vent PBG to the atmosphere at 55 cm $H_2O$, the safety vent 6 will vent PBG to the atmosphere once the pressure in the deformable reservoir reaches 60 cm $H_2O$.

The safety vent 6 may be constructed and arranged to continue venting PBG to the atmosphere until a corrective action is taken by the patient or healthcare provider. In one embodiment, the safety vent 6 may include a rupture member (e.g., a disc or panel) that bursts at a specified pressure and, thus, continues venting PBG to the atmosphere until the rupture disc is replaced.

In another embodiment, the safety vent 6 may include a pop safety valve that opens to vent PBG to the atmosphere when a maximum PBG pressure is reached inside of the deformable reservoir. After an overpressure condition in the deformable reservoir, the pop safety valve may remain in the open position until it is manually closed.

It should be recognized that the deformable section 22 may be constructed and arranged to include the function of the safety vent 6. That is, the deformable section 22 may be designed to rupture at a specific pressure and, thereby, continually vent PBG to the atmosphere until the deformable section 22 is replaced or repaired.

Figure 1B:
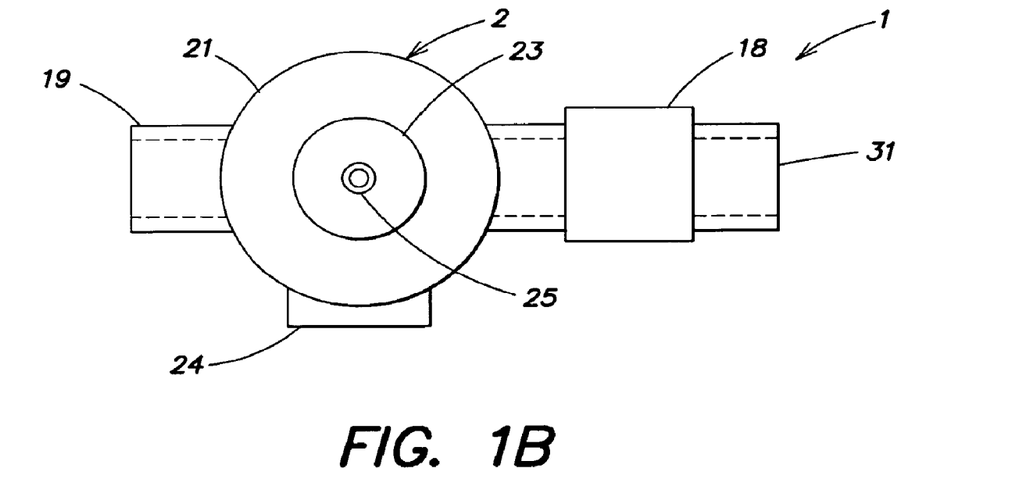
Figure 1C:
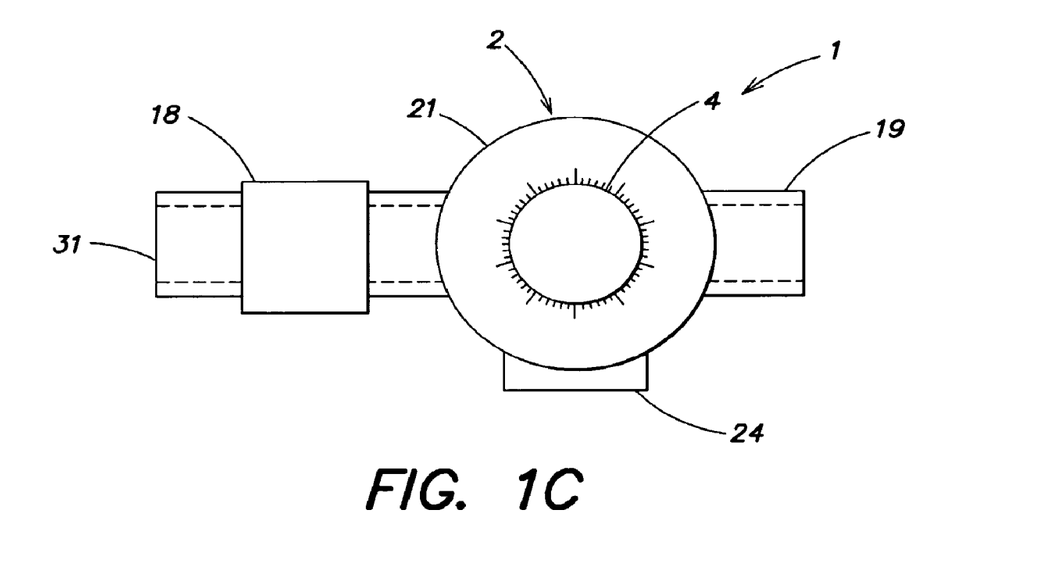

FIGS. 1B and 1C show left and right side views of the apparatus of FIG. 1A. FIGS. 1B and 1C illustrate embodiments of a PEEP valve (4), a pressurizing valve (18), an opening for a reservoir bag (19), a threaded opening for either a cap or a nebulizer (24), a connector for a compressed air source (25), and an opening for a mouthpiece (31).

Figure 2:
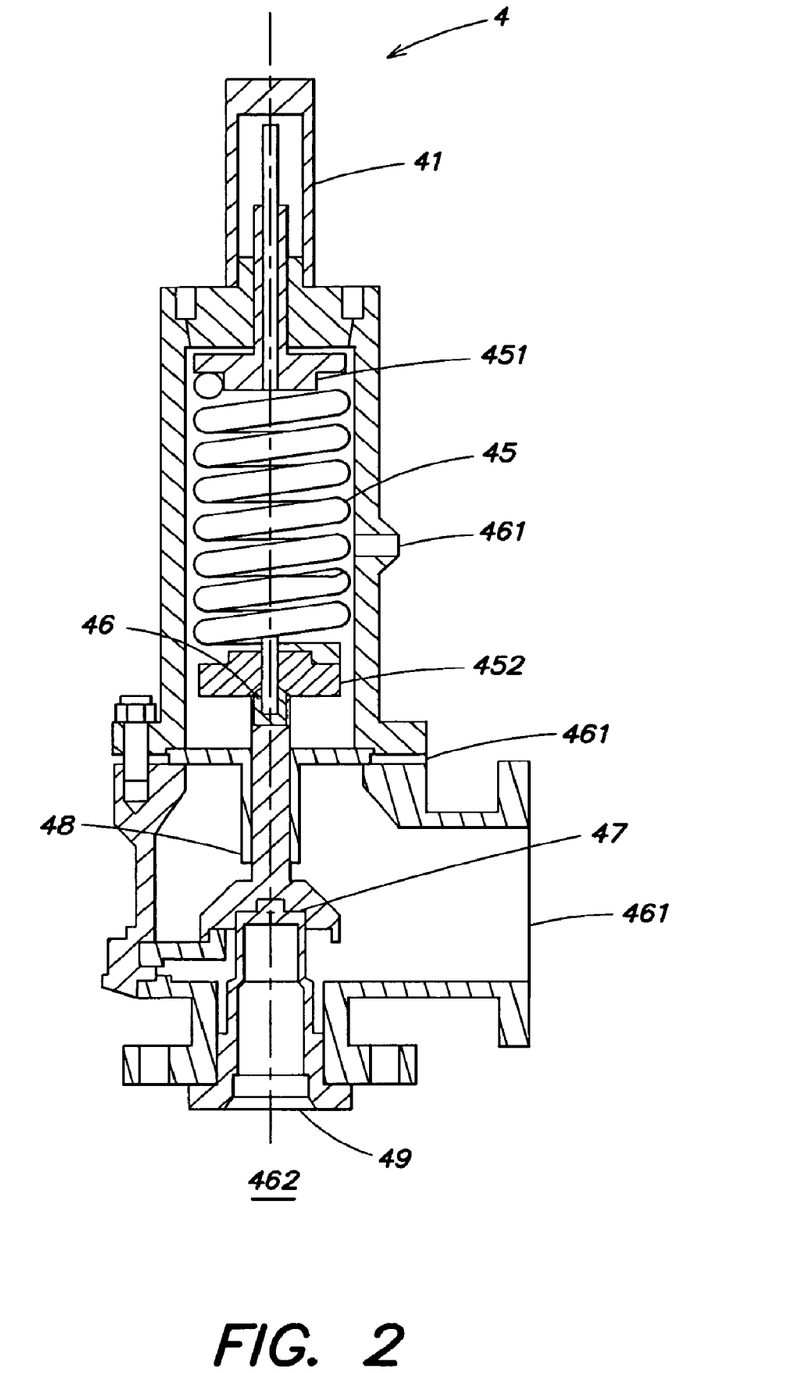
FIG. 2 shows a cross-sectional side view of a non-limiting embodiment of a pressure relief valve.

FIG. 2 is a cross-sectional view of an embodiment of a pressure relief valve 4. As shown in FIG. 2, pressure relief valve 4 may include a spring 45. In addition, a first end 451 of the spring 45 may be operably coupled to the adjuster 41 so that a user may vary the tension in the spring 45 by changing the position of the adjuster 41.

As is known in the art, varying the tension in the spring 45 also varies the venting pressure of the pressure relief valve 4. The second end 452 of the spring 45 may be in contact with a plunger 46. As shown in FIG. 2, the plunger 46 may be constrained to move along the longitudinal axis of a tube 48. In one embodiment, the position of the plunger 46 relative to a valve seat 47 may be controlled by the pressure differential between the spring pressure and the PBG pressure. In particular, the plunger 46 may move off of the valve seat 47, allowing PBG to escape to the environment through vent orifice 49, when the PBG pressure on the wet side 462 exceeds the spring pressure on the vent side 461. Similarly, the plunger 46 may remain in a leak tight contact with the valve seat 47, preventing PBG from venting to the environment through vent orifice 49, when the PBG pressure on the wet side 462 is less than the spring pressure on the vent side 461. It should be appreciated that any suitable pressure relief valve (e.g., a PEEP valve) may be used.

It should be understood that the devices of FIGS. 1-2 are only illustrative embodiments for delivering PBG to the airway of a patient with COPD. Other components achieving the same functional results also may be used.

In one embodiment, the respiratory assistance apparatus 1 may be operated as follows. Using a leak tight connection, a source of PBG 310 is placed in fluid communication with the opening 23 of the deformable reservoir 2. Next, the second opening 32 of the breathing interface 3 is placed in fluid communication with the airway of the patient through a substantially leak tight connection. A controlled flow of PBG may then be delivered to the deformable reservoir 2. However, alternatively, a controlled flow of PBG may be delivered to the deformable reservoir 2 before the breathing interface 3 is in fluid communication with the patient. In addition, an external apparatus such as a nebulizer or an MDI may be placed in fluid communication with the secondary orifice 24 of the deformable reservoir. With the breathing interface 3 in fluid communication with the patient's airway and a controlled flow of PBG flowing into the deformable reservoir, the venting pressure from the pressure relief valve 4 may be adjusted.

The venting pressure from the pressure relief valve 4 may be adjusted by adjusting the tension on the spring 45 and measuring the venting pressure in the deformable reservoir 2. Specifically, the pressure in the deformable reservoir 2 may be measured using a calibrated pressure transducer in fluid communication with the deformable reservoir 2. In this configuration, the venting pressure is the maximum pressure measured by the pressure transducer. To reach the target venting pressure, the pressure relief valve 4 may be initially set to have a low venting pressure, and the venting pressure may be progressively increased until the target venting pressure is achieved. For example, the pressure relief valve 4 may be adjusted to have an initial venting pressure of 1 cm $H_2O$, thereby allowing a user to increase the pressure in the deformable reservoir gradually until a target venting pressure of 10 cm $H_2O$ is achieved.

Alternatively, the pressure relief valve 4 may be pre-calibrated to allow a user to set the venting pressure of the apparatus without using a separate means of pressure measurement. Instead, the user may turn adjuster 41 to align pre-calibrated pressure markings with an indicator marker 42. For example, the user may select a venting pressure of 10 cm $H_2O$ by aligning a marker reading "10 cm $H_2O$" on adjuster 41 with an indicator marker 42.

With the venting pressure set and the breathing interface 3 in fluid communication with the airway of the patient, PBG may enter the deformable reservoir 2. The deformable section 22 of the deformable reservoir 2 may expand to contain a volume of PBG. The deformable reservoir 2 may be designed to expand to contain enough PBG to satisfy the breathing requirements of a patient. Thus, for example, the deformable reservoir 2 may be expandable to contain approximately one or more tidal volumes of a patient's breath.

When the pressure in the deformable reservoir 2 reaches the target venting pressure, PBG is vented from the deformable reservoir 2, through the pressure relief valve 4, and to the atmosphere. When the patient draws in a breath, PBG is delivered from the deformable reservoir 2 to the airway of the patient. Conversely, when the patient exhales, expired breath is delivered from the airway, through the breathing interface 3, and to the deformable reservoir 2.

If an external apparatus such as a nebulizer or MDI is in fluid communication with the deformable reservoir 2, medicine contained in the external apparatus may be delivered into the deformable reservoir 2. Consequently, as the patient draws in a breath, both PBG and medicine may be delivered from the deformable reservoir 2 to the airway of the patient.

Within the deformable reservoir 2, expired breath may mix with PBG to further increase the gas pressure within the deformable reservoir 2. One important aspect of the present invention is that the source of PBG 310 continually delivers pure PBG into the deformable reservoir 2, and the pressure relief valve 4 continually vents PBG (including expired breath) from the deformable reservoir. The resulting gas exchange within the deformable reservoir 2 ensures that the volume fraction of expired breath in the deformable reservoir 2 remains low enough (i.e., the oxygen in the deformable reservoir remains high enough) to support normal human respiration.

FIGS. 3-9 illustrate further embodiments of a respiratory assist device or components thereof. They can be used as described above. In general, a breathable gas source or means for providing breathable gas (e.g., at greater than atmospheric pressure) may be attached to a device illustrated in FIGS. 3-9 and used to provide positive respiratory pressure to a patient via a breathing piece (e.g., mouthpiece) attached to the device. FIGS. 3-9 illustrate embodiments of respiratory assist devices (RADs) of the invention and components or parts thereof. As discussed herein, different components or parts may be manufactured using any suitable material (e.g., plastic, glass, PVC, polymeric material, etc.). The material may be molded (e.g., injection molded), machined, or shaped using any suitable technique as the invention is not limited in this aspect. Individual components (e.g., a valve, a mouthpiece, a breathing bag, a nebulizer, a rigid section, a deformable section, etc., or any combination thereof) independently may be detachable, disposable, reusable, sterilizable, etc., or any combination thereof. Each component or part independently may be attached or connected using any suitable attachment or attaching means. For example, different components or parts may be connected via a screw (e.g., a separate screw that connects two pieces or the pieces may have threaded members that can screw together), a snap-fit, a tapered-fit, a latch, or any other mechanism (e.g., releasable or fixed). Components or parts may be connected directly or via a connector. An "O" ring or other suitable seal may be used to ensure that the connections are sufficiently air-tight. Certain components or parts may be connected using a glue (e.g., an epoxy glue). In some embodiments, a device or apparatus is manufactured as a single unit including all or most of the components described herein. In some embodiments, a device or apparatus may include all of the components or parts except for one or more of the mouthpiece, the valve (e.g., PEEP valve), or the breathing bag.

Figure 3A:
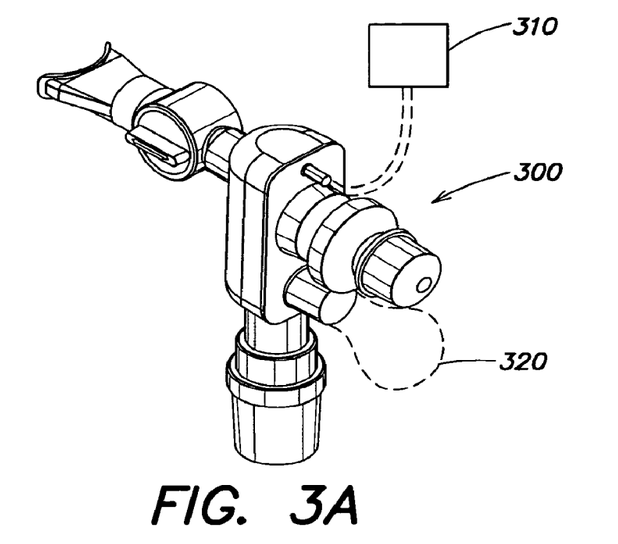
FIGS. 3A-C show different views of the device.
Figure 3B:
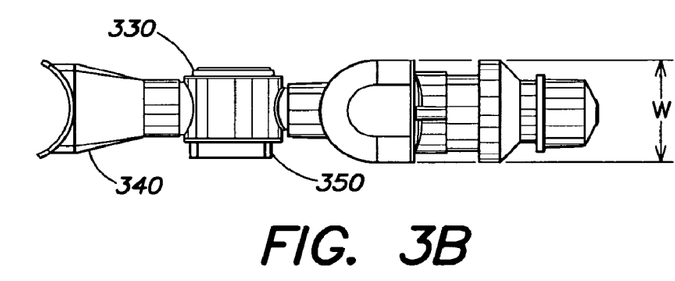
Figure 3C:
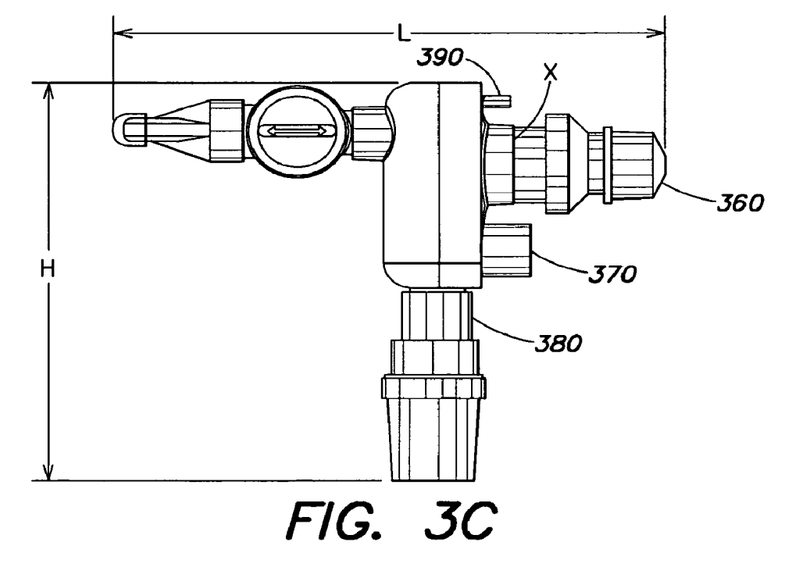
Figure 4A:
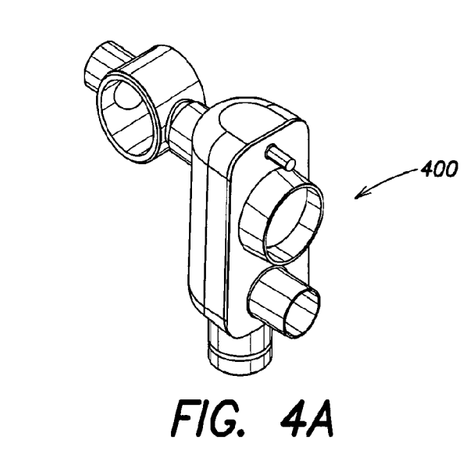
FIGS. 4A-D show different views of the sub-assembly.
Figure 4B:
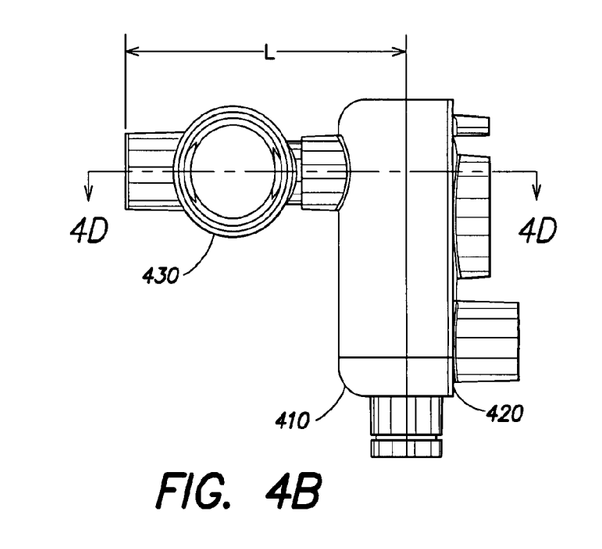
Figure 4C:
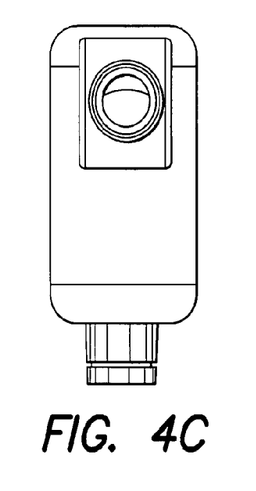
Figure 4D:
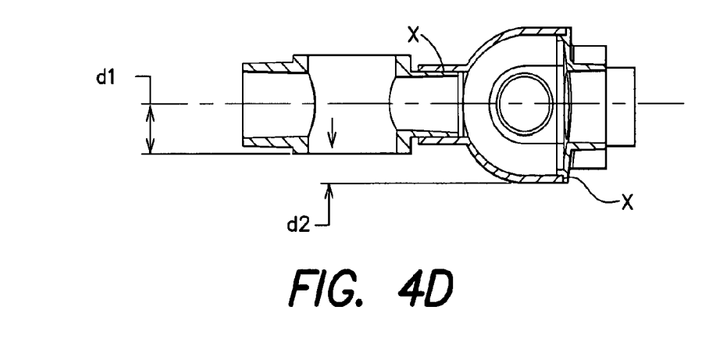
Figure 5A:
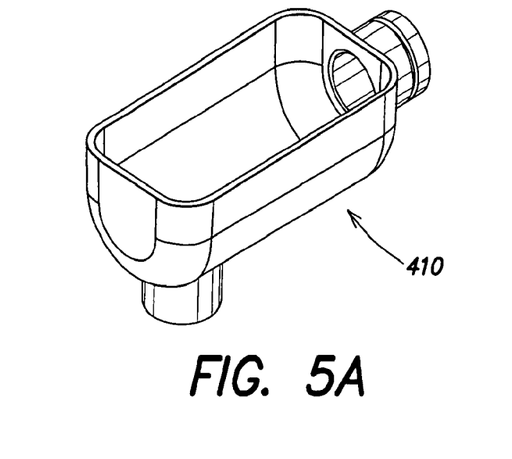
FIGS. 5A-D show different views of the body.
Figure 5B:
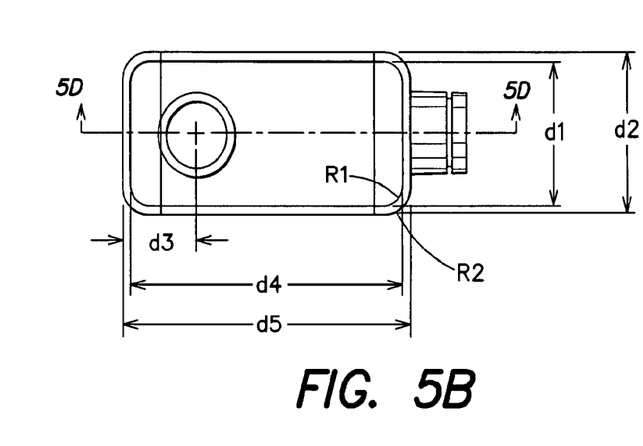
Figure 5C:
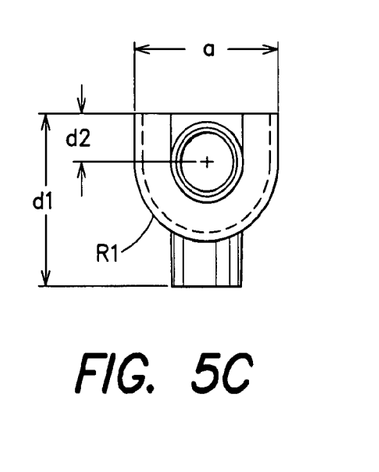
Figure 5D:
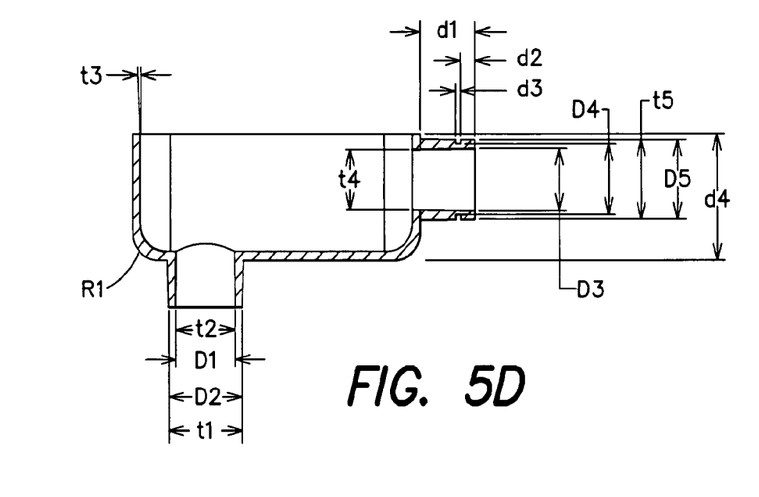
Figure 6A:
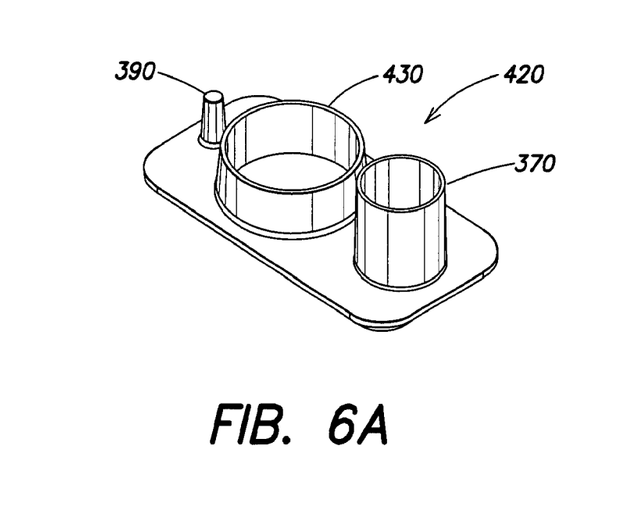
FIGS. 6A-D show different views of the cover.
Figure 6B:
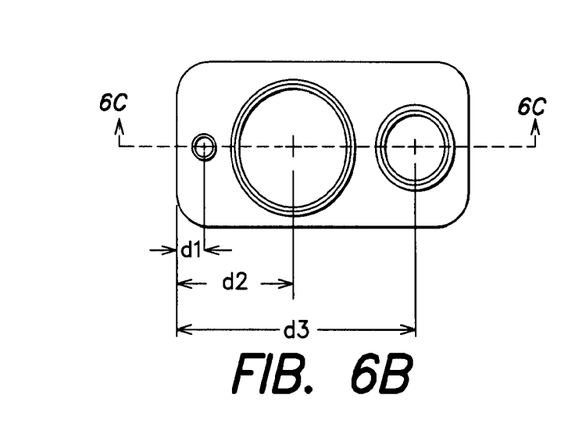
Figure 6C:
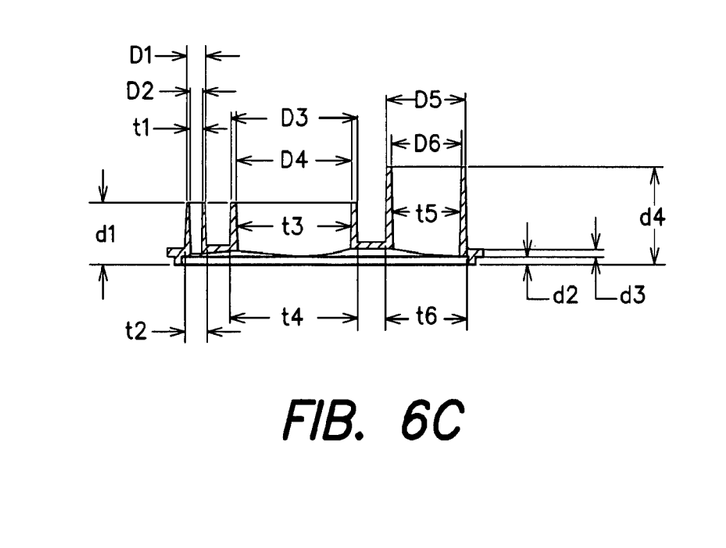
Figure 6D:
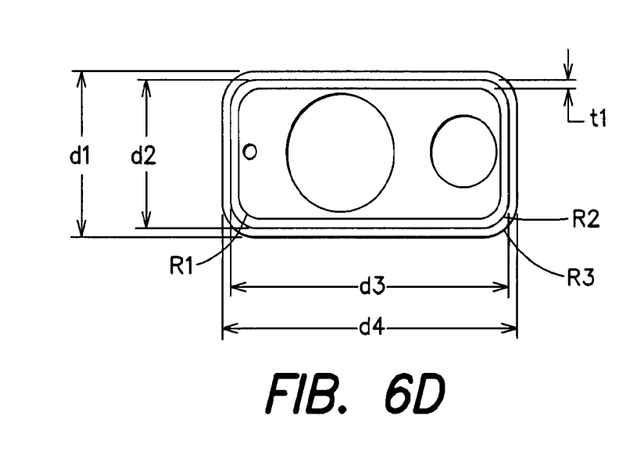
Figure 7A:
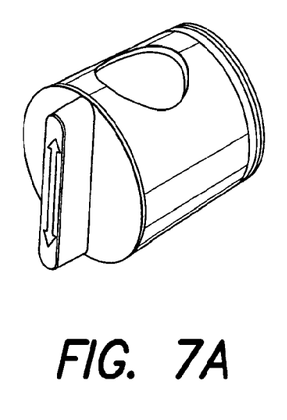
FIGS. 7A-D show different views of the valve.
Figure 7B:
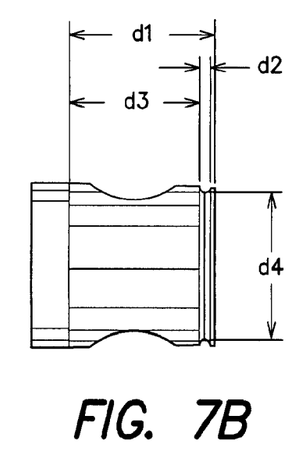
Figure 7C:
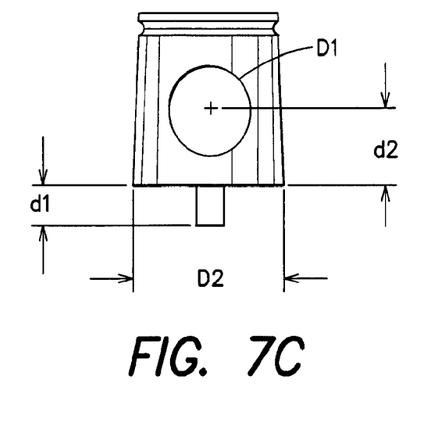
Figure 7D:
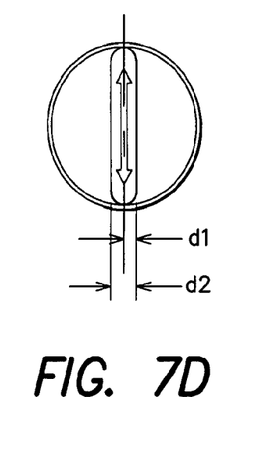
Figure 8A:
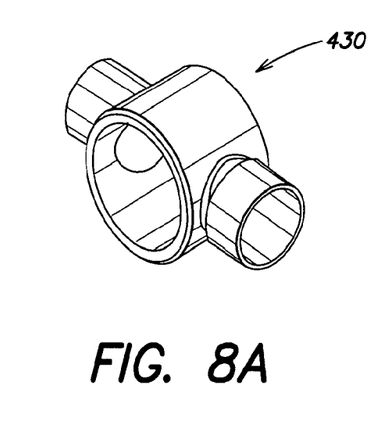
FIGS. 8A-D show different views of the housing; and, FIG. 9 illustrates an embodiment of a respiratory assist device body assembly fixture (900)
Figure 8B:
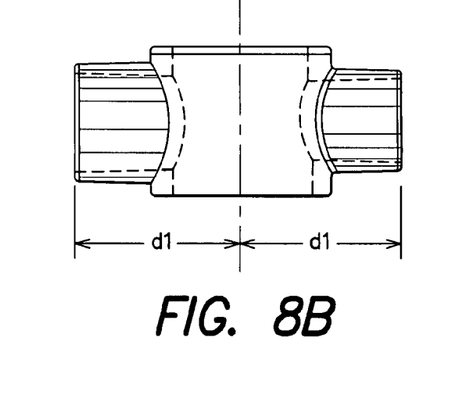
Figure 8C:
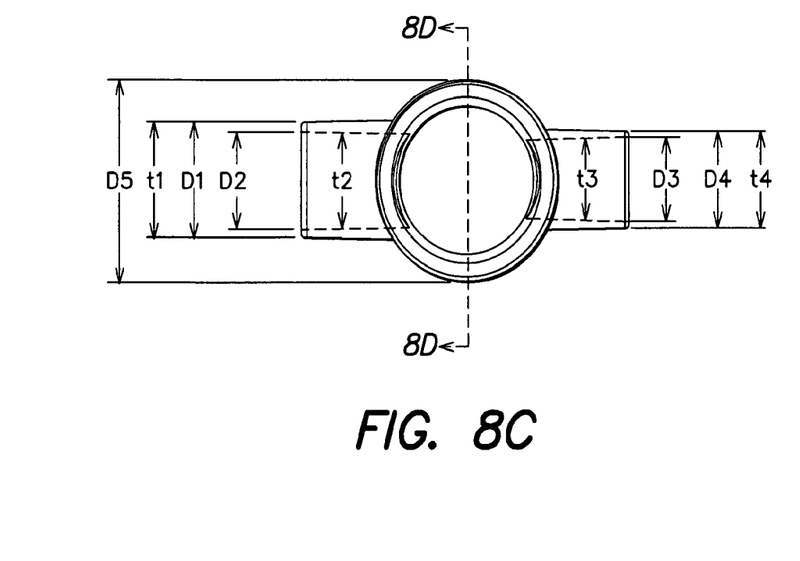
Figure 8D:
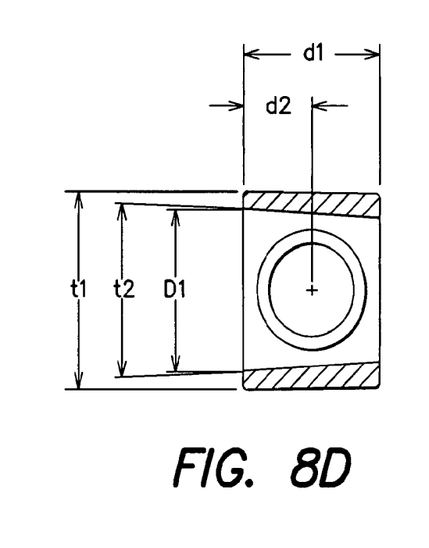

FIG. 3 shows an embodiment of a respiratory assist device (300). FIG. 3A shows a perspective view of a device connected to a source of breathable gas (310) and a deformable section (320) such as a bag. FIG. 3B shows a top view of the device of FIG. 3A, illustrating a breathing interface (340). In some embodiments, the breathing interface may be a mouthpiece (e.g., a disposable mouthpiece such as one available from Qosina, catalog number 55900). FIG. 3B also illustrates an O-ring (330) associated with a valve (350). The valve may include an O-ring (e.g., available from Parker, catalog number 2-120-S-70) as is illustrated in more detail below. However, other valve types or configurations may be used as the invention is not limited in this respect. FIG. 3C shows a side view of the device of FIG. 3A. A pressure relief valve (e.g., a PEEP valve) valve is illustrated in (360). A pressure relief valve may be disposable (e.g., a PEEP valve available from Ambu, catalog number 199-002-000. An optional drug nebulizer is illustrated in (380): An example of a nebulizer is a drug nebulizer (e.g., available from Qosina, catalog number 51060). It should be appreciated that one or more of these elements (breathing interface, valve, PEEP valve, nebulizer, or attachment for one or more thereof, etc.) may be detachable and optionally disposable. A location for a deformable section (for example, a breathing bag, e.g., a 1 liter breathing bag available from Qosina, catalog number 54926) is illustrated in (370). A location for attaching to a source of breathable gas (310) is shown at 390. It should be appreciated that the relative position of these features shown in FIG. 3 is illustrative only, as other configurations may be used. Dimensions of the assembly illustrated in FIG. 3 may be as follows. In FIG. 3B, width w may be 1.80 inches in some embodiments. In FIG. 3C, length l may be 8.5 inches in some embodiments and height h may be 6.8 inches in some embodiments. However, any other suitable dimensions may be used for the devices illustrated in FIG. 3 as the invention is not limited in this respect. Components may be attached using any suitable technique as described herein. For example, epoxy (e.g., EPO-TEK 301-2) may be applied to area X and allowed to cure (e.g., for 48 hours).

FIG. 4 shows an embodiment of a respiratory assist device sub-assembly (400). FIG. 4A shows a perspective view of the sub-assembly. FIG. 4B shows a side view illustrating a device body (410) and cover (420) and a valve housing (430). FIG. 4C shows a back view of the sub-assembly and FIG. 4D shows a top view of cross-section along line A-A of FIG. 4B. The valve housing may be connected to the device body at (X) using any suitable technique as described herein. Similarly, the body and cover may be connected (X) using any suitable technique. Dimensions of the sub-assembly illustrated in FIG. 4 may be as follows. In FIG. 4B, length l may be 3.63 in some embodiments. In FIG. 4D, dimensions d1 and d2, may be 0.56 and 0.33 inches respectively in some embodiments. However, any other suitable dimensions may be used for the devices illustrated in FIG. 4 as the invention is not limited in this respect.

FIG. 5 shows an embodiment of a respiratory assist device body (410) of FIG. 4. FIG. 5A shows a perspective view of the body. FIG. 5B shows a top view. FIG. 5C shows a right-side view, illustrating an opening for a nebulizer. It should be appreciated that this is optional. In some embodiments, a seal (e.g., a removable plug, lid, or other airtight sealing mechanism, e.g., using an O-ring) may be provided to seal the opening when a nebulizer is not attached. It should be appreciated that the nebulizer may be attached using any suitable means described herein. In some embodiments, an adaptor may be provided to allow attachment to one or more different nebulizers. FIG. 5D shows a cross-sectional side view along line A-A of FIG. 5B. Dimensions of the body illustrated in FIG. 5 may be as follows. In FIG. 5B, dimensions d1, d2, d3, d4, and d5 may be 1.640 (with tolerances of +0.008, −0.000), 1.80, 0.88, 3.344 (with tolerances of +0.008, −0.000), and 3.50 inches respectively in some embodiments. Radii R1 and R2 may be 0.36 and 0.44 inches in some embodiments. In FIG. 5C, dimensions d1 and d2 may be 1.90 and 0.52 inches respectively in some embodiments. Radius R1 may be 0.88 inches in some embodiments. Angle a may be 4.00° in some embodiments. In FIG. 5D, dimensions d1, d2, d3, and d4 may be 0.69, 0.18, 0.070 (with tolerances of +0.005, −0.000), and 1.40 inches respectively in some embodiments. Diameters D1, D2, D3, D4, and D5 may be 0.740, 0.870, 0.66, 0.750, and 0.864 inches respectively in some embodiments. Tapers t1, t2, t3, t4, and t5 may be 2.00°, 1.00°, 1.00°, 2.00°, and 1.00° respectively in some embodiments. However, any other suitable dimensions or angles may be used for the devices illustrated in FIG. 5 as the invention is not limited in this respect.

FIG. 6 shows an embodiment of a cover (420) of a respiratory assist device body of FIG. 4. FIG. 6A shows a perspective view of the cover. FIG. 6B shows a top view of the cover illustrating openings 370, 390 and 430, for a deformable member such as a breathing bag, a breathable gas supply, and a pressure relief valve, respectively. It should be appreciated that the relative locations and sizes of these openings is illustrative and is not intended to be limiting as other configurations may be used. FIG. 6C shows a side cross-sectional view along line A-A of FIG. 4B. As shown the openings have cylindrical walls that are tapered away from the cover and towards the end that is free for attachment to the respective components (e.g., gas provider, PEEP valve, air bag, etc.). Dimensions of the cover illustrated in FIG. 6 may be as follows. In FIG. 6B, d1, d2, and d3 may be 0.31, 1.38, and 2.86 inches respectively in some embodiments. In FIG. 6C, dimensions d1, d2, d3, and d4, may be 0.63, 0.09, 0.06, and 1.00 inches respectively in some embodiments. Diameters D1, D2, D3, D4, D5, and D6 may be 0.192, 0.150, 1.39, 1.295, 0.893, and 0.80 inches respectively in some embodiments. Tapers t1, t2, t3, t4, t5, and t6 may be 2.00°, 4.00°, 1.00°, 2.00°, 2.00°, and 1.00° respectively in some embodiments. However, any other suitable dimensions or angles may be used for the devices illustrated in FIG. 6 as the invention is not limited in this respect. Also, the walls of the openings are not required to be tapered and may be designed or manufactured to have other means of attachment as described herein. In some embodiments, the walls are straight and not tapered. In some embodiments, the walls are designed so that the device can be removably attached to one or more other components. However, in some embodiments, one or more other components may be fixed to the device (e.g., glued, fused, etc.). It should be appreciated that aspects of the device illustrated in FIGS. 4-6 relate to a device that is assembled from a plurality of component parts. However, devices of the invention may consist of a different configuration of smaller parts. For example, the body and cover of FIGS. 5 and 6 may be manufactured as a single piece (as opposed to being assembled from two pieces). However, other configurations of component parts are encompassed by the invention provided that they can be assembled or used to result in a device or method as described herein.

FIG. 7 shows an embodiment of a valve of a respiratory assist device of FIG. 3. FIG. 7A shows a perspective view of the valve. FIG. 7B shows a side view of the valve. FIG. 7C shows a top view of the valve. FIG. 7D shows a left-side view of the valve. The valve illustrated in FIG. 7 can be used with a device as illustrated in FIG. 3. However, it should be appreciated that different types of valves (e.g., manually operated valves, electrically controlled valves, or other types of valves may be used). Dimensions of the valve illustrated in FIG. 7 may be as follows. In FIG. 7B, d1, d2, d3, and d4 may be 1.260, 0.094 (with tolerances of +0.005, −0.000), 1,125 (with tolerances of +0.001, −0.001), and 1.045 inches respectively in some embodiments. In FIG. 7C, d1 and d2 may be 0.30 and 0.56 inches respectively in some embodiments. Diameters D1 and D2 may be 0.69 and 1.248 (with tolerances of +0.001, −0.001) respectively in some embodiments. In FIG. 7D, dimension d1 and d2 may be 0.10 and 0.20 respectively in some embodiments. However, any other suitable dimensions or angles may be used for the devices illustrated in FIG. 7 as the invention is not limited in this respect.

FIG. 8 shows an embodiment of a valve housing of a respiratory assist device. The valve housing of FIG. 8 can be used with the valve of FIG. 7 and attached to a device as illustrated in FIG. 3. FIG. 8A shows a perspective view of the valve housing. FIG. 8B shows a top view of the housing indicating the outer dimensions by a solid line and the inner dimensions by a dotted line. FIG. 8C shows a right side view and FIG. 8D shows a cross-sectional view along line A-A of FIG. 8C. The openings illustrated in FIG. 8 are formed by cylinders having tapered walls. Dimensions of the valve housing illustrated in FIG. 8 may be as follows. In FIG. 8B, d1 may be 1.38 inches in some embodiments. In FIG. 8C, diameters D1, D2, D3, D4, and D5 may be 0.897, 0.75, 0.640, 0.73, and 1.54 inches respectively in some embodiments. Tapers t1, t2, t3, and t4 may be 1.00°, 2.00°, 2.00°, and 1.00° respectively in some embodiments. In FIG. 8D, dimension d1 and d2 may be 1.125 (with tolerances of +0.002, −0.002) and 0.56 respectively in some embodiments. Diameter D1 may be 1.250 (with tolerances of +0.003, −0.003) in some embodiments. Tapers t1 and t2 may be 2.00° and 6.00° respectively in some embodiments. However, any other suitable dimensions or angles may be used for the devices illustrated in FIG. 8 as the invention is not limited in this respect.

Figures 9A, 9B, 9C, 9D:
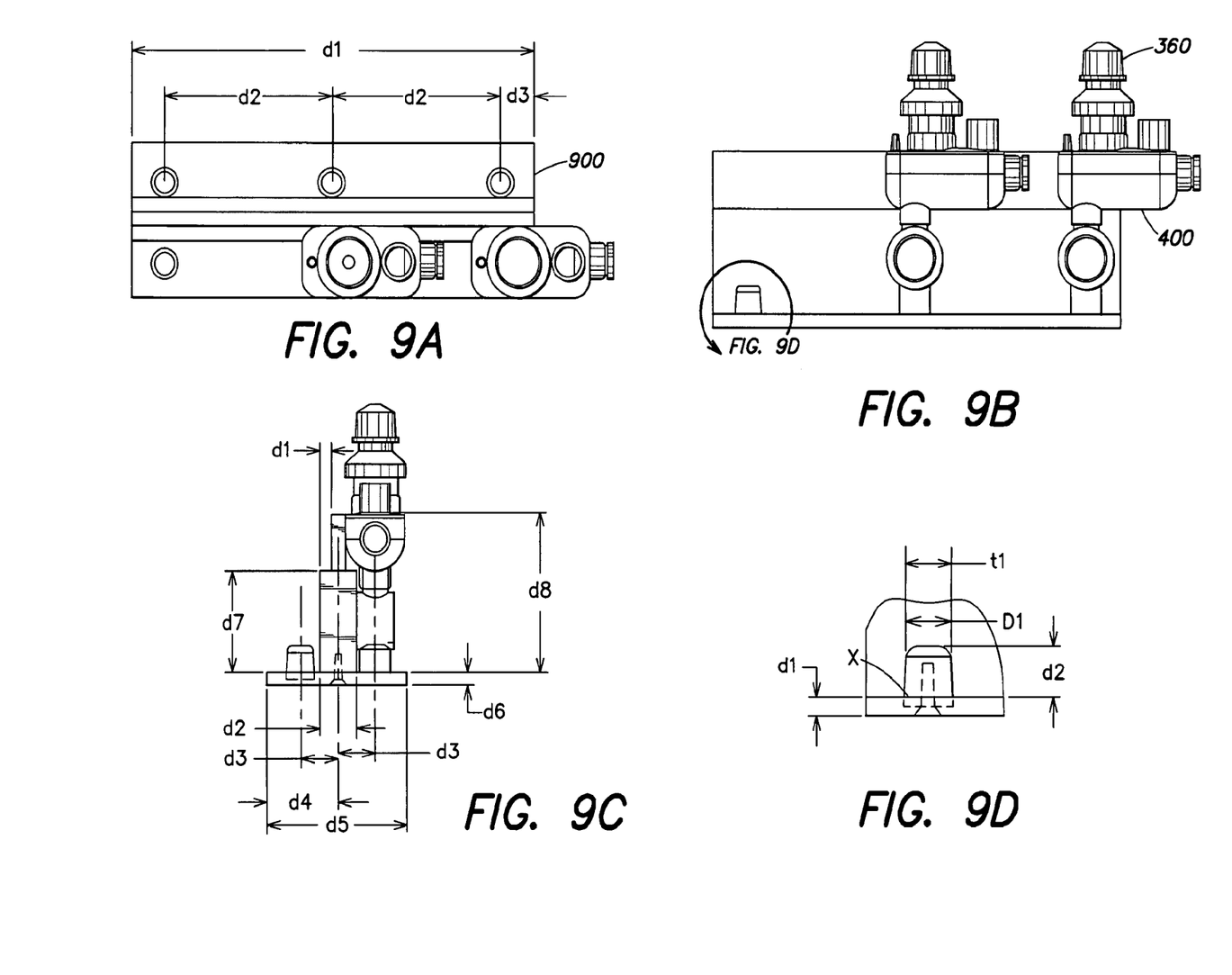
FIGS. 9A-D show different views of the fixture.

FIG. 9 shows an embodiment of an assembly fixture device (900) that can be used to assemble respiratory assist devices of the invention. FIG. 9A shows a top view of a device with six positions for assembling devices. However, other numbers of assembly places may be used as the invention is not limited in this respect. Two devices being assembled are shown in FIGS. 9A, B, and C. FIG. 9B shows a side view of the assembly fixture showing the two devices being assembled. In this embodiment, the devices being assembled are position on a support via the free opening of the valve body (the opening that is not attached to the device body). However, other configurations may be used as the invention is not limited in this respect. FIG. 9C shows an end-view of the assembly fixture showing central wall with an open position on the left side of the wall and a device being assembled on the right side of the wall. The wall as illustrated is shaped to accommodate and/or support different components of a device being assembled. However, other shapes or configurations may be used. FIG. 9D illustrates a position where a cylindrical support is designed to fit into the opening of the valve body as illustrated in FIGS. 9A-C. However, it should be appreciated that a position may include a support that can fit into an alternative opening (e.g., gas intake, PEEP valve opening, bag opening, nebulizer opening, etc.) depending on the configuration that is used to assembled a device of the invention. Dimensions of the fixture illustrated in FIG. 9 may be as follows. In FIG. 9A, dimensions d1, d2, and d3 may be 12.00, 5.00, and 1.00 inches respectively in some embodiments. In FIG. 9C, dimensions, d1, d2, d3, d4, d5, d6, d7, and d8 may be 0.335, 1.00, 1.075, 2.00, 4.00, 0.25, 2.75, and 4.25 inches, respectively in some embodiments. In FIG. 9D, dimensions d1 and d2 may be 0.13 and 0.75 inches respectively in some embodiments. Diameter D1 may be 0.750 inches in some embodiments. Taper t1 may be 2.00° in some embodiments. However, any other suitable dimensions or angles may be used for the devices illustrated in FIG. 9 as the invention is not limited in this respect. It should be appreciated that the assembly fixture of FIG. 9 can be used to assemble devices from a plurality of parts (e.g., two or more) as described herein. However, in some embodiments, a device may be produced as a single piece (e.g., molded, and/or machined, etc.) that does not need assembling.

Accordingly, it should be appreciated that a device of the invention may be a single body construction (e.g., molded, for example injection molded) or may be assembled from component parts that are attached (e.g., detachably via a screw, clip, friction via tapered joints, or in some embodiments permanently e.g., glued welded or any other suitable attachment technique as described herein). One or more components may be molded and/or machined as described herein.

Accordingly, certain aspects of the invention relate to one or more component parts of a respiratory assist device described herein (e.g., alone, for example individually packaged, or provided together, for example attached together or packaged together but not preassembled). Other aspects of the invention relate to methods of using a respiratory assist device (e.g., for patients suffering from certain acute or chronic respiratory conditions).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A handheld breathing assistance device to reduce respiratory muscle fatigue in a user with obstructive lung disease, the device comprising:

a deformable reservoir adaptable for containing pressurized breathing gas, at least a portion of the deformable reservoir being constructed and arranged to change shape to vary the volume of the pressurized breathing gas contained within the deformable reservoir;

a breathing interface for delivering pressurized breathing gas from said deformable reservoir to the airway of the user, the breathing interface being adaptable for fluid communication with the airway of the user, the breathing interface being further adaptable for fluid communication with the deformable reservoir;

at least one pressure relief valve to control the pressure of the gas contained in the deformable reservoir, the at least one pressure relief valve having an inlet and an outlet, the inlet being adaptable to be in fluid communication with the deformable reservoir, the outlet being adaptable to be in fluid communication with the atmosphere.

2. The device of claim 1 further comprising a means for creating fluid communication between the deformable reservoir and a source of the pressurized breathing gas.

3. The device of claim 2, wherein the means for creating fluid communication includes a threaded tube connector.

4. The device of claim 2, wherein the means for creating fluid communication includes a barbed tube connector.

5. The device of claim 2 further comprising a source of pressurized breathing gas.

6. The device of claim 5, wherein the source of pressurized breathing gas is a pressurized gas bottle.

7. The device of claim 5, wherein the source of pressurized breathing gas is a pump that increases the gas pressure within the deformable reservoir by drawing air from the atmosphere into the deformable reservoir.

8. The device of claim 7, wherein the pump is hand-operated.

9. The device of claim 1, wherein the deformable reservoir is expandable to a total volume between 10 to 750 ml greater than the total volume of said deformable reservoir under atmospheric pressure.

10. The device of claim 1, wherein the deformable reservoir includes a balloon.

11. The device of claim 1, wherein the deformable reservoir includes a diaphragm.

12. The device of claim 1 further comprising a means for adjusting the maximum expanded volume of the deformable reservoir.

13. The device of claim 1, wherein the breathing interface includes a mouthpiece couplable to the mouth of the user.

14. The device of claim 1, wherein the breathing interface includes a mask that fits over the nose and mouth of the user.

15. The device of claim 1, wherein the at least one pressure relief valve includes a one-way valve, said one-way valve preventing pressurized breathing gas from venting to the atmosphere when the pressurized breathing gas contained within the deformable reservoir is below a target venting pressure and venting the pressurized breathing gas to the atmosphere when the pressurized breathing gas contained within the deformable reservoir is equal to or above said target venting pressure.

16. The device of claim 1, further comprising an adjuster for varying the pressure of the gas contained in the deformable reservoir.

17. The device of claim 16, wherein said adjuster includes a spring and wherein the tension of the spring is varied to change the venting pressure of the gas contained in the deformable reservoir.

18. The device of claim 1, wherein the at least one pressure relief valve is positioned downstream of the breathing interface to facilitate venting expired air from the deformable reservoir.

19. The device of claim 1 further comprising a secondary orifice, the secondary orifice being adaptable to fluid communication with an external apparatus and further adaptable to fluid communication with the deformable reservoir.

20. The device of claim 19, wherein the external apparatus is a nebulizer.

21. The device of claim 19, wherein the external apparatus is a metered dose inhaler.

22. The device of claim 1 further comprising a multi-conduit mixing volume, the multi-conduit mixing volume including one conduit adaptable for connection to the deformable reservoir, a second conduit adaptable for connection the breathing interface, a third conduit adaptable for fluid communication with the source of pressurized gas, and a mixing volume adaptable to be in fluid communication with each conduit.

23. The device of claim 22, wherein the multi-conduit mixing volume includes a T-connector, the centerlines of the first and second conduits being axially aligned and the centerline of the third conduit being perpendicular to the axis of the centerlines of the first and second conduits.

24. The device of claim 22, wherein the multi-conduit mixing volume further includes a fourth conduit adaptable for detachably connecting a nebulizer, wherein the fourth conduit is adaptable to be in fluid communication with the mixing volume.

25. A method of reducing respiratory muscle fatigue comprising:
coupling the airway of a user in fluid communication with a breathing interface;
accepting pressurized gas into a deformable reservoir that is in fluid communication with the breathing interface;
allowing the deformable reservoir to expand to contain a desired volume of pressurized gas;
delivering the pressurized gas to the airway of the user through the breathing interface; and
venting the gas from the deformable reservoir when the pressure in the deformable reservoir exceeds a predetermined threshold.

26. The method of claim 25, wherein the source of pressurized gas is oxygen.

27. The method of claim 25, wherein the source of pressurized gas is a mixture of oxygen and at least one inert gas.

28. The method of claim 25 further comprising accepting expired gas from the user through the breathing interface.

29. The method of claim 25 further comprising coupling an external apparatus to a secondary opening, the secondary opening being adaptable to fluid communication with the deformable reservoir and further adaptable to fluid communication with the breathing interface.

30. The method of claim 29 wherein the external apparatus is a nebulizer.

31. The method of claim 29 wherein the external apparatus is a metered dose inhaler.

32. The method of claim 29 further comprising delivering the contents of the external apparatus to the user through the breathing interface.

33. The method of claim 25 further comprising varying the venting pressure of the gas stored in the deformable reservoir.

34. The method of claim 25 further comprising varying the maximum expanded volume of the deformable reservoir.

* * * * *